United States Patent [19]

Shilo et al.

[11] Patent Number: 4,693,842
[45] Date of Patent: Sep. 15, 1987

[54] CYANOBACTERIUM-PRODUCED BIOEMULSIFIER COMPOSITION AND SOLUTION THEREOF

[75] Inventors: Moshe Shilo, Jerusalem; Ali Fattom, Maale Hagalil, both of Israel

[73] Assignees: Solmat Systems, Ltd., Yavne; Yissum Research Development Company of the Hebrew University of Jerusalem, Jerusalem, both of Israel

[21] Appl. No.: 731,002

[22] Filed: May 6, 1985

Related U.S. Application Data

[63] Continuation-in-part of Ser. No. 634,535, Jul. 26, 1984, Pat. No. 4,649,110.

[51] Int. Cl.$^4$ ............... B01F 17/30; B01F 17/34
[52] U.S. Cl. .................... 252/356; 210/925; 252/8.551; 252/174.24; 252/312; 426/54; 435/84; 435/264; 435/271
[58] Field of Search ............ 252/312, 356, 8.551, 252/174.24; 435/87, 101

[56] References Cited

U.S. PATENT DOCUMENTS

| | | | |
|---|---|---|---|
| 2,732,661 | 1/1956 | Spoehr et al. | 47/1.4 |
| 2,908,113 | 10/1959 | Martin | 47/1.4 |
| 3,208,526 | 9/1965 | Patton et al. | 166/246 |
| 3,346,463 | 10/1967 | Goren | 435/101 |
| 3,374,081 | 3/1968 | Miller | 71/11 |
| 3,406,114 | 10/1968 | Goren | 210/730 |
| 3,432,427 | 3/1969 | Moore | 210/601 |
| 3,598,730 | 8/1971 | Nordgren et al. | 210/725 |
| 3,681,283 | 8/1972 | Yueh et al. | 210/606 |
| 3,684,706 | 8/1972 | Bomstein | 210/606 |
| 3,732,089 | 6/1973 | Megronigle | 47/1.4 X |
| 3,763,039 | 10/1973 | Wilson | 210/625 |
| 3,820,281 | 6/1974 | Bigler et al. | 47/58 |
| 3,850,799 | 11/1974 | Ludwig | 210/730 |
| 3,889,418 | 6/1975 | Porter et al. | 47/58 |
| 3,958,364 | 5/1976 | Schenck et al. | 435/101 |
| 4,078,331 | 3/1978 | Savins et al. | 435/101 |
| 4,078,332 | 3/1978 | Savins | 435/101 |
| 4,079,544 | 3/1978 | Savins | 435/101 |
| 4,087,936 | 4/1978 | Savins et al. | 47/1.4 |
| 4,235,043 | 11/1980 | Harasawa et al. | 47/1.4 |
| 4,236,349 | 12/1980 | Ramus | 47/1.4 |
| 4,253,271 | 3/1981 | Raymond | 47/1.4 |
| 4,311,829 | 1/1982 | Gutnick et al. | 252/356 X |
| 4,320,594 | 3/1982 | Raymond | 47/1.4 |
| 4,341,038 | 7/1982 | Bloch et al. | 47/1.4 |
| 4,417,415 | 11/1983 | Cysewszi et al. | 47/1.4 |

OTHER PUBLICATIONS

Research Thesis by ZUR entitled "Interaction Between Algae and Inorganic Suspended Solids".
Abimelech et al., (Science, vol. 216, Apr. 2, 1982, pp. 63–65).

Primary Examiner—Richard D. Lovering
Attorney, Agent, or Firm—Sandler & Greenblum

[57] ABSTRACT

J-1 which is a strain of cyanobacteria is used to form and excrete a material useful as an emulsifying agent for forming emulsions of hydrocarbons and oils in liquids such as water.

Method of separating and culturing the cyanobacteria under conditions necessary to achieve a maximum formation and excretion of the emulsifying agent into solution.

Method of purifying and separating excreted as well as intracellular material from cyanobacteria.

Method of removing stains with a material excreted by cyanobacteria, and particularly strain J-1.

Method of effecting the secondary recovery of petroleum through the use of a material excreted by cyanobacteria, and particularly strain J-1.

Extracellular polymeric material which is greater than 200,000 Daltons in molecular weight, and contains sugar, fatty acid, and protein moieties, and amide, carboxylic and amino groups.

8 Claims, 7 Drawing Figures

FIG. 1.

FIG. 7.
IR SPECTRUM OF EMULCYAN

CYANOBACTERIUM-PRODUCED BIOEMULSIFIER COMPOSITION AND SOLUTION THEREOF

APPLICATION STATUS

This application is a continuation-in-part of U.S. application Ser. No. 634,535 filed July 26, 1984, now U.S. Pat. No. 4,649,110 the disclosure of which is hereby incorporated by reference.

BACKGROUND OF THE INVENTION

1. Field of the Invention

The invention relates to a method of separating bacteria from a liquid, and to a method for culturing the bacteria to produce a polymer useful as an emulsifying agent. The invention further relates to the polymeric substance produced, and to methods of using the polymeric substance.

2. Description of Pertinent Materials

Many situations exist in which it is desirable to utilize an emulsifying agent to disperse one substance in another. More particularly, an emulsifying agent is often used to disperse a hydrocarbon material or oil into another medium, such as water.

The number of situations in which it is desirable to utilize an emulsifying agent to disperse various types of oils or hydrocarbons are many and varied. For example, emulsifying agents may be used in the dispersal of oils in various types of food preparations, in the secondary recovery of petroleum, and as a stain remover.

A large portion of valuable petroleum is not recovered from wells through pumping techniques, because the oil or other material sticks to the surface of dirt particles. An emulsifying agent can loosen the trapped petroleum, which can then be recovered. Emulsifying agents are also useful in the cleaning of residual oils from oil tankers, in the preparation of alcohol-oil mixtures for use as fuels, and in the dispersion of oil spills or slicks on bodies of water.

It is currently customary to use manufactured chemical preparations as emulsifying agents. Such materials are often quite expensive.

It would, therefore, be desirable to use as emulsifying agents materials which could be readily and inexpensively produced or secured from natural sources.

SUMMARY OF THE INVENTION

It is an object of the invention to provide a process for the production of a novel emulsifying agent, useful in the emulsification of hydrocarbons and oils.

The objective of the invention is achieved through the use of cellular products of a benthic filamentous cyanobacterium of Phormidium genus in the family Oscillatoriaceae. This strain has been found to exist in a portion of the Jordan river, where it was noticed that the water seemed to be clarified of its particulates, as discussed in patent application Ser. No. 634,535, filed July 26, 1984, and now U.S. Pat. No. 4,649,110, of which this application is a continuation-in-part. One particular bacterial strain of Phormidium useful in the invention has been denominated as J-1. J-1, is, in effect, a definite strain of an undefined species of the Phormidium genus. A specimen of this organism has been deposited with the American Type Culture Collection in Rockville, Md., and has been assigned ATCC No. 39161. This strain has a generation time of 24–48 hours, and under the carefully controlled conditions of the invention, the organism produces and excretes a polymeric bioemulsifying material which is useful in achieving the objectives of the invention. The polymeric bioemulsifier can also be secured from the bacterial cells themselves, by rupturing the cells and then isolating the bioemulsifying agent.

The organisms of the invention are found naturally in certain fresh water bodies. These organisms can be collected and removed from the water for culturing, according to the inventive technique, by adding nonpolar hydrocarbons into the water containing the bacteria, and agitating the water to disperse the hydrocarbon into globules, as described in U.S. application Ser. No. 634,535, now U.S. Pat. No. 4,649,110 discussed above. Because benthic bacteria (including members of the Phormidium genus) are hydrophobic, the bacteria become attached to the dispersed globules of hydrocarbon. The hydrocarbon is collected as it floats to the water surface, and the bacteria can then be separated from the hydrocarbon and grown under laboratory conditions.

Once the hydrocarbons have been separated according to the inventive technique, separated cyanobacteria are ready for treatment according to another aspect of the invention.

Under specially controlled and tailored growth conditions, using properly selected media, and under defined physiological conditions, the cyanobacteria of the invention can be made to produce and excrete effective amounts of a polymeric substance useful as an emulsifying agent, and referred to in this application as a emulcyan.

According to the invention, the bacteria produce emulcyan towards the end of an exponential growth phase and excrete the active, high-molecular-weight substance into the external milieu during a subsequent stationary phase. This substance is extremely effective as an emulsifying agent.

For the exponential growth phase to occur, the microorganisms must be provided with an adequate amount of light, ideally ranging from 20 to 30 $\mu E/m^2/sec^{-1}$. The temperature should range between about 27°–33° C. The mineral requirements of the organisms are preferably met by using a Chu-11 medium which is made as described in the scientific article entitled "Hydrophobicity as an Adhesion Mechanism of Benthic Cyanobacteria" by Ali FATTOM and Moshe SHILO (Applied and Environmental Microbiology, January 1984, Vol 47, No. 1 pp.135–143.

The bioemulsifier described in this invention has a molecular weight above 200,000 Daltons. Chemical analysis indicates that it contains sugar, fatty acid and protein moieties. Enzymatic degradation of 70% of the protein content does not affect the emulsification activity. Infrared spectrophotometry indicates that the bioemulgent contains amide, carboxylic and amino groups.

The bacteria are subjected to careful growth conditions so as to produce effective concentrations of the bioemulsifier. The bacteria are first subjected to conditions necessary to achieve an exponential growth condition as discussed in the parent application. This treatment is continued for approximately six days until the bacteria begin to produce increased levels of the bioemulsifier towards the end of the six day period. Exponential growth is then stopped and the bacteria are made to enter a resting phase by reducing the calcium ion concentration in the solution from about 35 mg/l to about 350 mg/liter. During this phase, effective levels of the polymer are excreted into the surrounding solution.

Although the entire crude bacteria-containing solution may then be used as an emulsifying agent, according to one embodiment of the invention, the bioemulsifier is separated from the remainder of the solution. The separation may be performed by centrifuging the cell culture, such that a first pellet (or filtrate) is produced, along with the corresponding supernatant. Both the pellet and the supernatant are subjected to a series of treatment steps to provide maximum recovery. The first pellet formed as mentioned above will yield the cell-bound bioemulsifier, which had not yet been excreted by the bacteria, while the supernatant will yield the extracellular bioemulsifyer which had already been excreted into the culture medium before the original centrifugation.

Likewise, as discussed in the parent application Ser. No. 634,535, now U.S. Pat. No. 4,649,110 the first pellet will also yield the cell-bound bioflocculant, while the supernatant will also yield the extracellular bioflocculant, when subjected to the series of treatment steps. In the above-mentioned parent application, a series of treatment steps is described for producing two pellets of bioflocculant. Subsequent study has shown that these two corresponding supernatants also contain the bioemulsifier of the present invention. This bioemulsifier can be separated from its solution by flash evaporation.

Although the above technique is cell destructive, the invention likewise optionally includes techniques in which only the original supernatant is treated to remove the bioemulsifier, while the pellet containing the cells is reused by being subjected to another exponential growth phase.

BRIEF DESCRIPTION OF THE DRAWINGS

The above objectives, features and advantages of the present invention will be more fully apparent to those of ordinary skill in the art to which this invention pertains from the accompanying drawings, wherein.

DETAILED DESCRIPTION

The bacteria of the invention have been found in nature and may be cultured either in the laboratory or in their natural environment to produce the inventive composition.

When it is desired to obtain a concentrated sample of the inventive bacteria from their environment in bodies of water, the bacteria are separated from their natural environment and then may be cultured under controlled conditions.

Separation may be performed by means of a filtration or by centrifugation separation techniques.

According to a liquid-liquid separation technique of the invention, one or more non-polar water immiscible hydrocarbons such as xylene, heptane, octane, hexadecane, and mixtures thereof, are added to the bacteria-containing body of water and agitated to form globules. By virtue of the non-polar nature of the hydrocarbons, benthic bacteria (including some members of the Phormidium genus, particularly the J-1 strain) will be adsorbed onto the hydrocarbon globules by virtue of their hydrophobic nature. By dispersing the hydrocarbon into small globules, improved separation is achieved. This occurs by virtue of the improved liquid-liquid contact, providing a greater effective globule surface area. Depending upon the nature of the environment, various agitation and/or mixing techniques may be used to accomplish this purpose.

After sufficient agitation, the hydrocarbon material with the J-1 adhering thereto is separated from the liquid. The hydrocarbon globules, such as heptane, may be collected by centrifugation or filtration and then separated. The bacteria are then separated from the hydrocarbon phase by any one of a number of standard techniques. For example, small scale separation may be achieved by filtration of the bacteria cells on glass microfiber filters. On a large scale other filtration techniques may be used.

It should be noted that other hydrophobic bacteria, other than strain J-1, which may be present in the original liquid environment, may also unavoidably be removed by means of the liquid-liquid separation technique referred to above, when the bacteria are found in an uncontrolled non-laboratory environment. When this is the case, the J-1 strain is preferably subsequently separated from the undesired bacteria when a pure culture is desired, through isolation of individual cells by methods known to those skilled in the art.

Once the bacteria have been collected, and are in a medium where variables can be controlled, the bacteria may then be conditioned so as to produce effective amounts and concentrations of the emulsifying agent.

The bioemulgent is preferably prepared in the following manner:

Cyanobacteria of Phormidium genus (strain J-1) do not ordinarily produce sufficient quantities of the described emulcyan. The production of large amounts of the bioemulgent is dependent upon the physiological state of the organism. To achieve sufficient production, the organism must be allowed to proceed from an exponential growth phase, to a late phase of stationary growth. During this exponential growth phase the proper nutrients must be readily available. The nutrients are preferably provided by using a Chu-11 medium. Essential materials include nitrogen and phosphate as well as light and carbon dioxide from the atmosphere. The temperature range is preferably between 27°–33° C.

Figure 2:
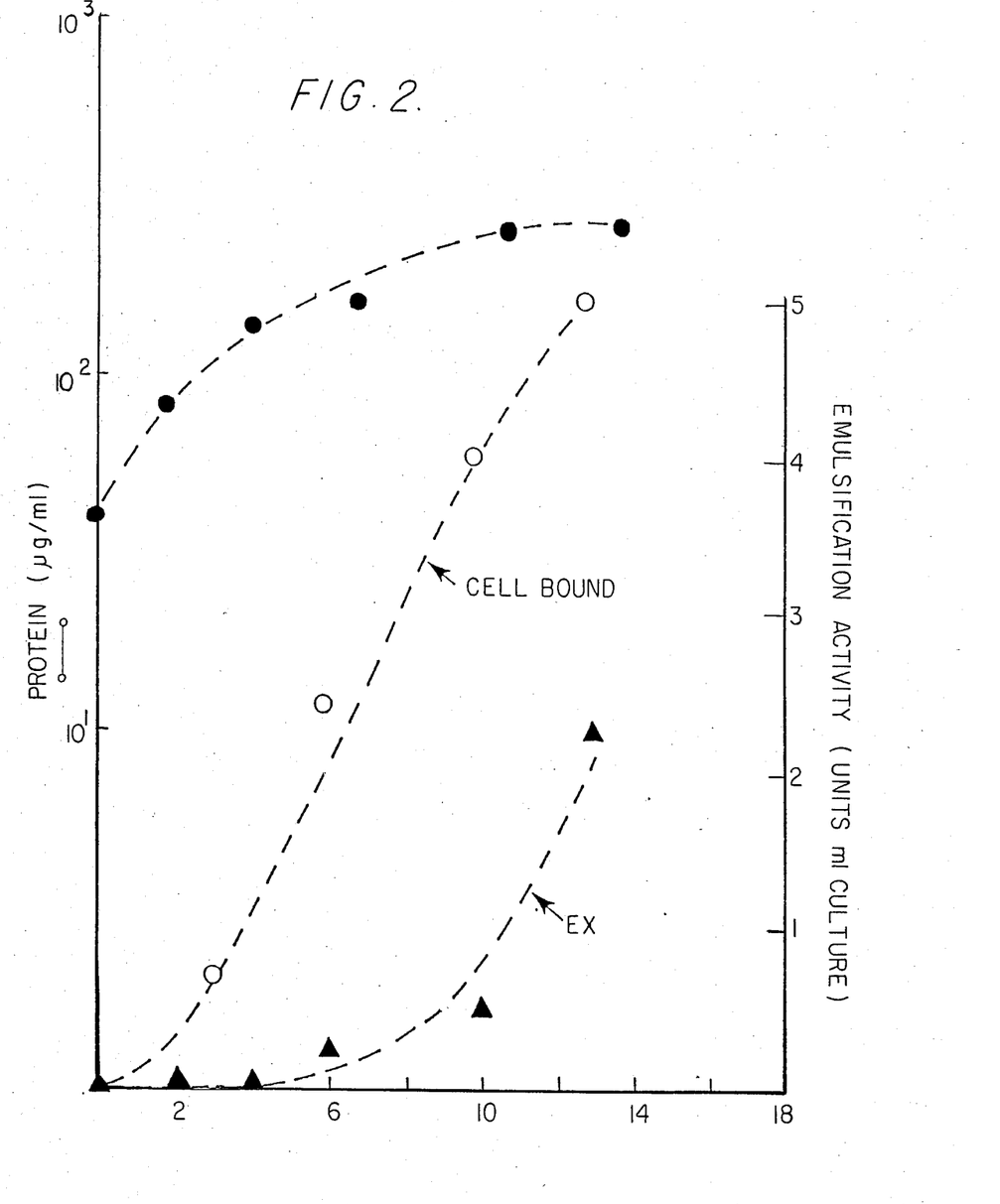
FIG. 2 is graph showing production of cell-bound and extracellular emulcyan, as a function of time in days, in cultures of Phormidium, with the amount of protein (i.e., the quantity of cells produced) plotted on the left ordinate as a function of time in days, and emulsification activity shown on the right ordinate.

As may be seen from FIG. 2, the exponential growth phase requires about twelve days, during which time the cell protein increases to about $10^2$ µg/ml. The production of cell-bound bioemulgent shows a regular steady increase almost from the outset. However, the production of extracellular bioemulgent does not show a sharp increase until about the eighth day of culture.

As in the case of the bioflocculant of U.S. application Ser. No. 634,535, now U.S. Pat. No. 4,649,110 the amount of bioemulgent produced and excreted into the solution is markedly increased by lowering the available level of calcium ions in the culture medium, in order to subject the organisms to a state of relative deprivation of calcium, such that the organisms enter a dormant phase. Peak production of the bioflocculant of the above-mentioned parent application and the emulcyan of the present invention occurs at the same time.

Calcium deprivation may be achieved either by limiting the amount of calcium added to, or present in the solution containing the microorganism, or by adding a chelating agent such as EDTA.

As the emulcyan is partially free in the culture medium, it is possible to use the culture medium directly to emulsify the hydrocarbons and oils. However, it is most effective to separate the bioemulsifier from the Phormidium. This is done by a series of steps, whereupon the bioemulgent and the bioflocculant described in the parent application are separated from the bacteria. The separation of these substances is achieved as described below.

Figure 6:
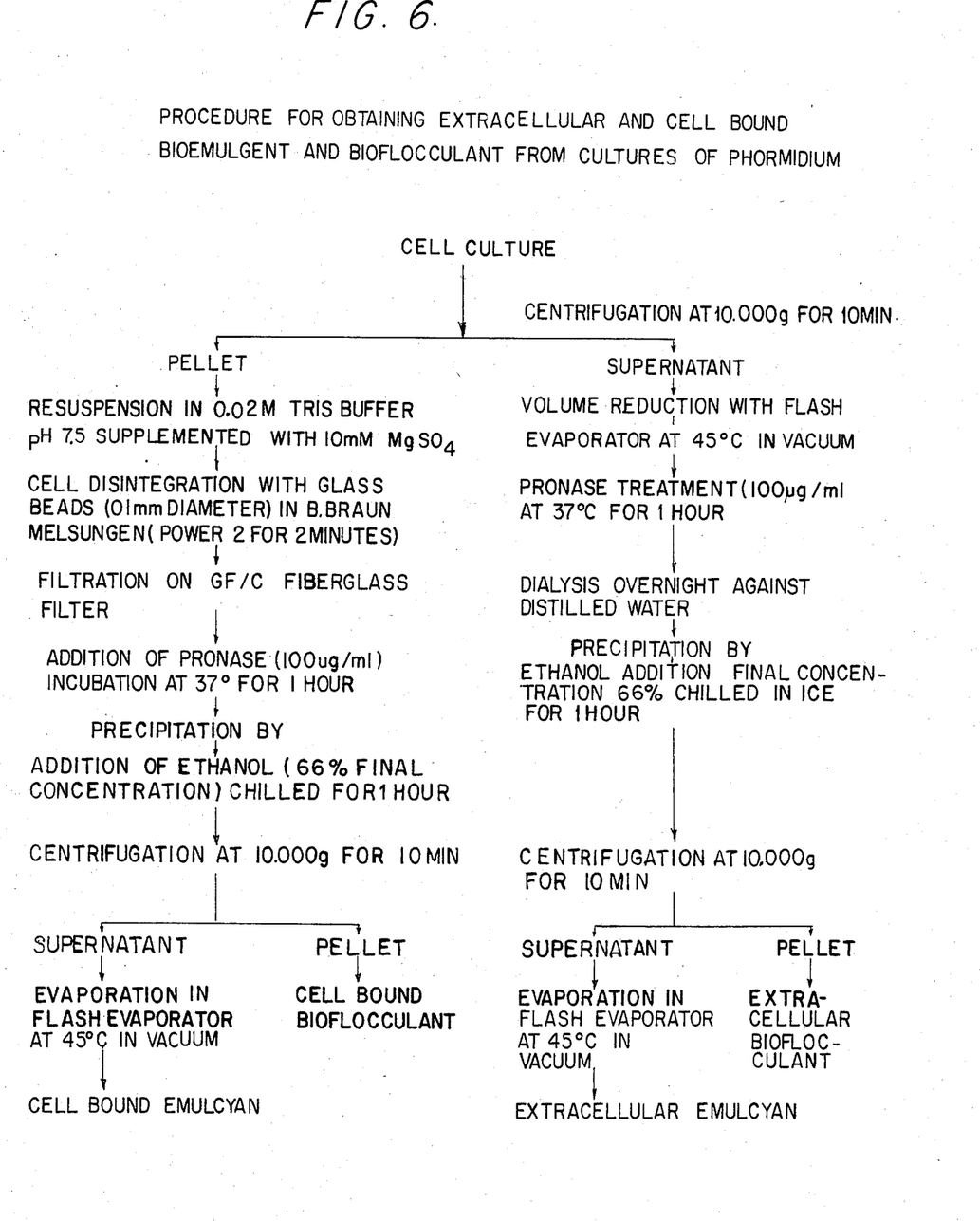
FIG. 6 is a flow chart showing the treatment steps of the process of the invention for isolating extracellular and cell-bound emulcyan (and also bioflocculant) from cultures of Phormidium.

As illustrated in FIG. 6, the cell culture is first subjected to centrifugation at 10,000 g for 10 minutes to produce an initial pellet and an initial supernatant.

The pellet is resuspended in 0.02 M Tris buffer solution at a pH of 7.5, supplemented with 10 mM $MgSO_4$. The cells in this solution are then subjected to disintegration by treatment with glass beads of 0.1 mm in diameter in a B. Braun Melsungen agitator maintained at power level 2 for two minutes. The resulting solution with the broken cells is then subjected to filtration on a GF/C fiberglass filter. Pronase (produced by the Sigma Company) is then added to the filtrate in the amount of 100 μg/ml of filtrate. (Pronase is a non-specific proteolytic enzyme formed by *Steptomyces griseus.*) This mixture is incubated at 37° C. for one hour. Ethanol is then added at 66% final concentration to effect precipitation, and the mixture is chilled in ice water for one hour, after which it is subjected to centrifugation at 10,000 g for 10 minutes.

As a result, a second supernatant and a second pellet are produced. The pellet is treated as described in the parent application to isolate the cell-bound bioflocculant, while the supernatant is subjected to evaporation in a flash evaporator at 45° C., in a vacuum, to isolate the cell-bound bioemulsifier.

The initial supernatant produced by the original centrifugation of the cell culture described above is subjected to volume reduction with a flash evaporator at 45° C. in a vacuum. The concentrated supernatant is then subjected to Pronase treatment at a concentration of 100 μg/ml at 37° C. for one hour, and subjected to dialysis for approximately 8 hours against distilled water, whereupon ethanol is added, to a final concentration of 66%, and the mixture is chilled in ice water for one hour. The addition of ethanol causes precipitation of extracellular bioflocculant. The solution is then subjected to centrifugation at 10,000 g for 10 minutes, to produce a supernatant and pellet. The pellet constitutes one part of the bioflocculant discused in the parent application, as mentioned above. The supernatant is subjected to evaporation in a flash evaporator at 45° C. in a vacuum to isolate the extracellular bioemulgent.

Clearly, the treatment of the initial pellet resulting from the original centrifugation of the cell culture is cell destructive, and requires that a fresh batch of microorganism be provided if the production of the bioemulgent is to be repeated. However, where it is desired that the microorganisms be reused, the cells clearly should not be destroyed. Cells can be taken from the dormant phase and reconditioned by the proper treatment and can once again undergo exponential growth, whereby the process can be repeated. If it is decided to destroy the cells, the destroyed cells can be used as animal feed.

It should be noted that the technique illustrated in FIG. 6 provides a method for removing any intracellular bioemulsifier remaining within the microorganisms. Although it is preferable to first subject the microorganisms containing increased levels of emulcyan to a stationary phase which results in the excretion of the bioemulsifier, if, for some reason, the microorganisms are not subjected to the stationary phase, the cells containing increased levels of emulcyan may simply be destroyed to recover the intracellular emulcyan.

Figure 7:
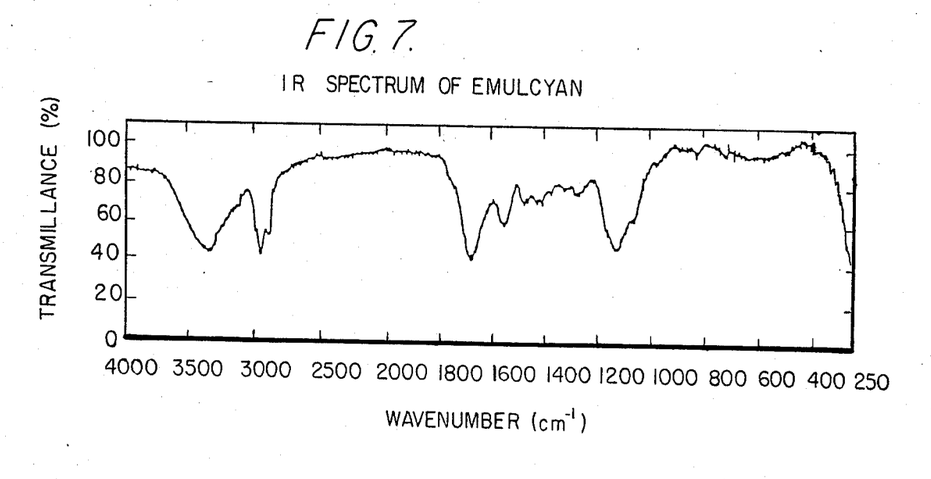
FIG. 7 is a reproduction of the IR spectrum of the emulcyan, with a listing of functional groups shown to be present in the bioemulsifier.

The bioemulsifier of the invention has a molecular weight above 200,000 Daltons. Chemical analysis indicates that it contains sugar, fatty acid and protein moieties. Enzymatic degradation of 70% of the protein content does not affect the emulsification activity. Infrared spectrophotometry indicates that the emulcyan contains amide, carboxylic and amino groups. FIG. 7 is a reproduction of the IR spectrum associated with the emulcyan, listing the functional groups whose presence is indicated.

To determine the emulsification activity of the emulcyan, varying quantities of it were mixed into a 0.02 M Tris buffer at a pH of 7.5, supplemented with 10 mM $MgSO_4$. The final volume of each mixture was 7.5 ml in 125 ml Erlenmeyer flasks. Following this, 0.1 ml of a mixture of hexadecane and 2-methylnaphthalene (1 to 1 volume to volume) was added, and each flask was shaken for 1 hour at 150 strokes per minute at room temperature. The suspension was then read in a Klett-Summerson colorimeter at 540 nm. One unit of emulsification activity gave a 13.3 Klett unit increase in the optical density reading.

Figure 5:
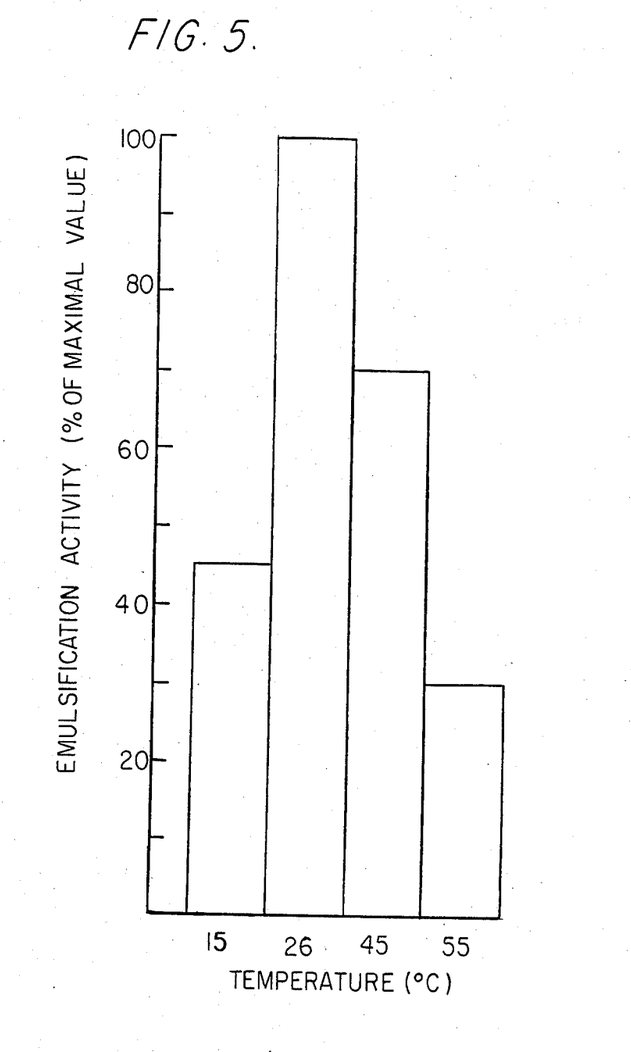
FIG. 5 is a bar graph which illustrates the effect of temperature on emulsification activity of bioemulgent.

As seen from FIG. 5, emulsification activity is temperature dependant, and is shown to be at 100% of maximal value at a temperature of approximately 26° C. Temperatures lower or higher than this ideal temperature cause the bioemulsifier to exhibit a lower emulsification activity. For example, at 15° C. the emulsification acitivity is 45% of maximal value. At 55° C., the emulsification activity is 30% of maximal value. The experimental procedure used to generate the data for FIG. 5 is the same as that utilized for FIG. 3, discussed below, except that the mixtures were shaken at the appropriate temperatures.

Figure 3:
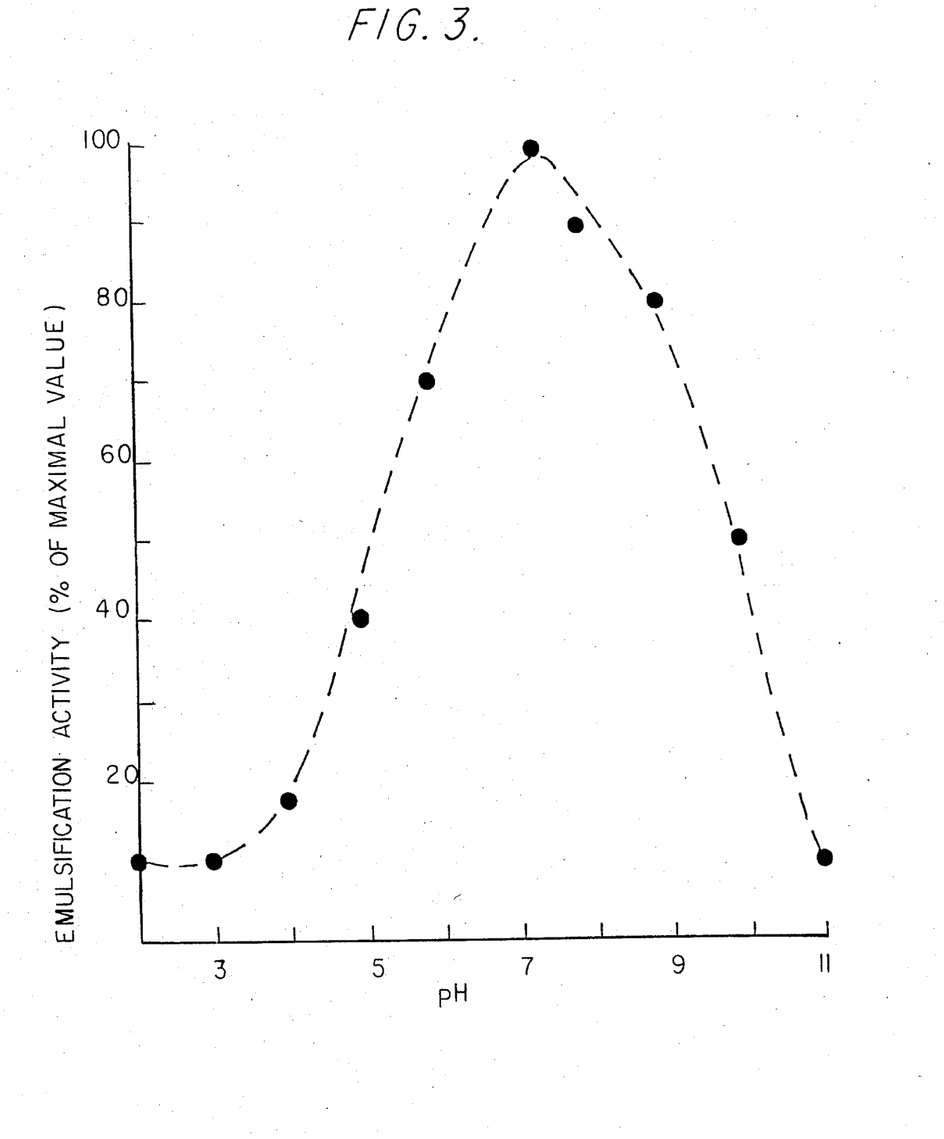
FIG. 3 is a graph illustrating the effect of pH on the emulsification activity of strain J-1 purified bioemulgent (E. J-1)

To test the effect of pH on the emulsification activity of the emulcyan (as shown in FIG. 3) 65 g/ml of the emulcyan were dissolved in a 0.02 M Tris buffer, supplemented with 10 mM $MgSO_4$. To this solution, 0.1 ml of a mixture of hexadecane and 2-methylnaphthalene (one to one, volume to volume) was added. The final volume was 7.5 ml in a 125 ml flask. NaOH or HCl were added to obtain the appropriate pH. The flasks were shaken 150 strokes per minute at 26° C. for 1 hour. The turbidity of the resulting emulsion was measured in a Klett-Summerson colorimeter at 540 nm.

As shown in FIG. 3, the emulsifying agent is effective over a wide range of pH values, and may preferably be used at a pH value of anywhere from about 3.0 to 11.0. However, emulsification activity is pH dependent, and, as may be seen from FIG. 3, the emulcyan is most effective at a pH of about 5-9. The values shown in FIG. 3 are expressed as a percent of maximal value.

Figure 1:
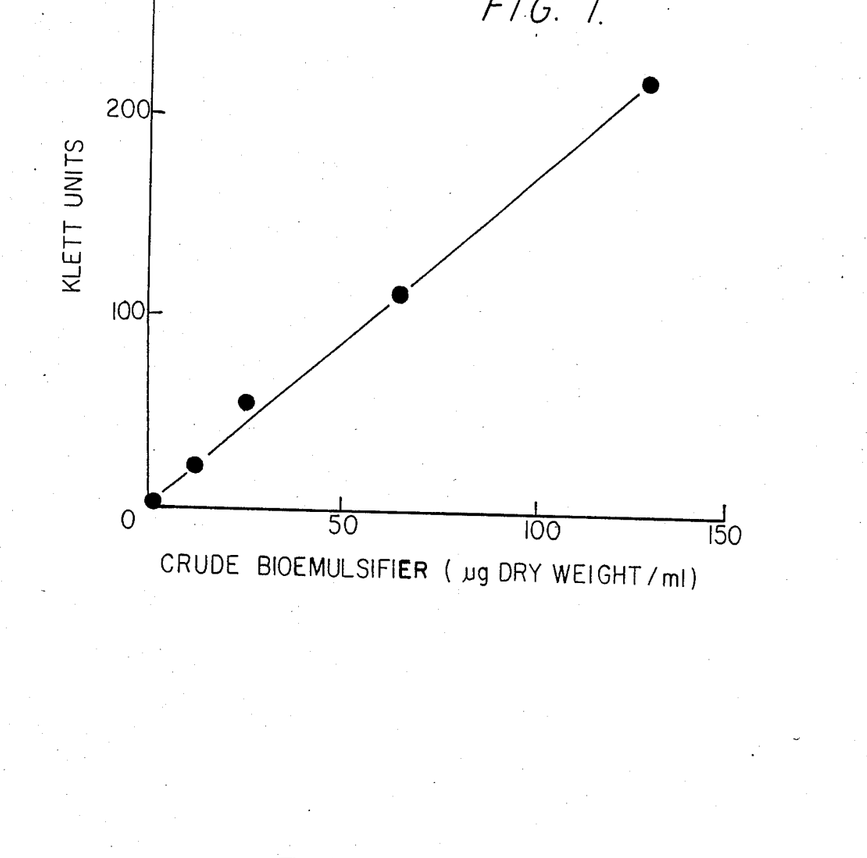
FIG. 1 is a graph plotting emulsification activity (in Klett units) as a function of emulcyan concentration.

The activity level of the emulcyan is dose dependent (see FIG. 1). However, there is no clear optimum concentration. As seen from FIG. 1, emulsification activity (in Klett units) shows a steady increase as the crude bioemulgent concentration increases. This is unlike the performance of the bioflocculant discussed in the above-mentioned parent application, where there is an optimum concentration, at which flocculation activity reaches a peak.

In testing the emulsification activity of the bioemulgent, as shown in FIG. 1, different concentrations were prepared from purified emulcyan in a 0.02M Tris buffer with a pH of 7.5, supplemented with 10 mM of $MgSO_4$.

Figure 4:
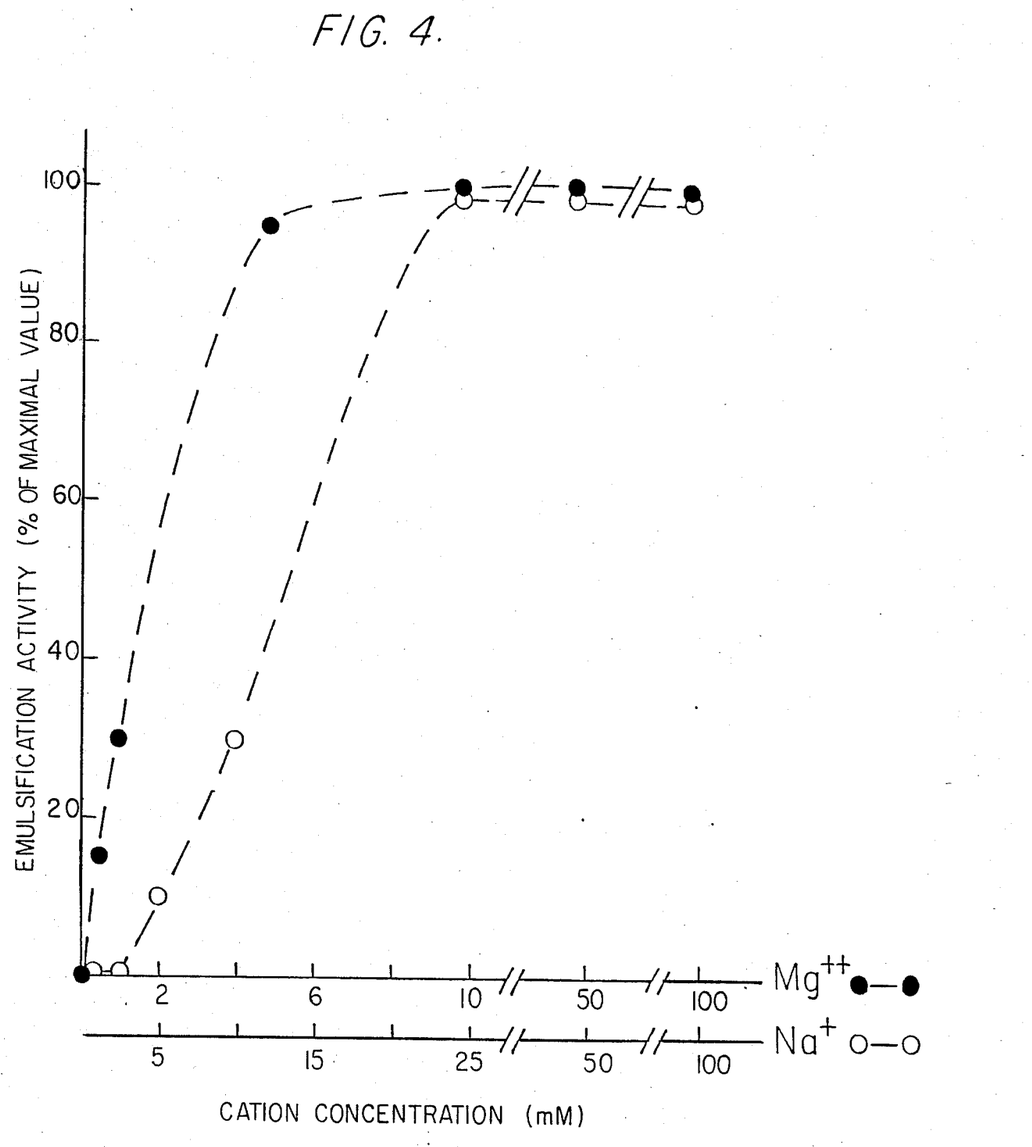
FIG. 4 is a graph illustrating the effect of magnesium and calcium cation concentration on emulsification activity of emulcyan.

As illustrated in FIG. 4, the emulsification activity of the emulcyan (as a percentage of maximal value) is dependent upon cation concentration in the medium being treated. FIG. 4 indicates, that with $Mg^{2+}$, optimal concentration is around 4.0 mM, whereas the optimal concentration for $Na^+$ is reached at approximately 25 mM. Up to each of these two points, the presence of increasing concentrations of these two cations results in a regular and sharp increase in emulsification activity. After the emulsification activity reaches 100% of its maximal value, additional quantities of cation will only cause the emulsification activity to stay at 100% of maximal value. However, excess quantities of cations will not do any harm to emulsification activity. The buffer used in connection with the experiments related to FIG. 4 is the same as that utilized in connection with FIG. 3, with the exception that the buffer was supplemented with the appropriate concentration of cations. The data for FIG. 4 were generated under ideal conditions of temperature (26° C.) and pH (7.5).

FIG. 2 illustrates the production, as a function of time, of cell bound and extracellular bioemulsifier, as well as cellular protein, in cultures of Phormidium. Phormidium J-1 cells are innoculated into a Chu-11 medium and the culture is incubated in an illuminated shaker at 150 strokes per minute, at a light intensity of 20 $\mu E/m^{-2}/sec^{-1}$. Samples are then taken periodically for the determination of extracellular and cell bound emulsification activity. Cellular protein is determined by the Lowry method.

It is believed that the advantages and improved results furnished by the method of the present invention are apparent from the foregoing descriptions of the preferred embodiment of the invention. Various changes and modifications may be made without departing from the spirit and scope of the invention as described in the claims that follow.

What is claimed is:

1. A treatment solution containing an extracellular substance formed by a cyanobacterium, having a molecular weight greater than 200,000 Daltons, containing sugar, fatty acid and protein moieties, and amide, carboxylic and amino groups, in an effective concentration capable of causing substantial emulsification of a liquid hydrocarbon into a second liquid.

2. The substance as defined by claim 1 wherein said cyanobacterium is a benthic bacterium.

3. The substance as defined by claim 1 wherein said cyanobacterium is a member of the Phormidium genus.

4. The substance as defined by claim 3 wherein said member of the Phormidium genus is strain J-1.

5. A bioemulsifier composition comprising a substance formed from a cyanobacterium having a molecular weight greater than 200,000 Daltons, containing sugar, fatty acid and protein moieties, and amide, carboxylic and amino groups capable of causing substantial emulsification of a liquid hydrocarbon into a seocnd liquid.

6. The bioemulsifier composition in accordance with claim 5, wherein said cyanobacterium is benthic bacterium.

7. The bioemulsifier composition in accordance with claim 5, wherein said cyanobacterium is a member of the Phormidium genus.

8. The bioemulsifier composition in accordance with claim 7, wherein said member of the Phormidium genus is strain J-1.

* * * * *